(12) United States Patent
Marino et al.

(10) Patent No.: US 9,516,762 B2
(45) Date of Patent: *Dec. 6, 2016

(54) SOLDERING IRON WITH AUTOMATIC SOLDERING CONNECTION VALIDATION

(71) Applicant: DELAWARE CAPITAL FORMATION, INC., Wilmington, DE (US)

(72) Inventors: Kenneth D. Marino, Long Beach, CA (US); Hoa Nguyen, Santa Ana, CA (US)

(73) Assignee: OK International Inc., Garden Grove, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/794,678

(22) Filed: Jul. 8, 2015

(65) Prior Publication Data
US 2016/0031044 A1    Feb. 4, 2016

Related U.S. Application Data

(60) Provisional application No. 62/033,037, filed on Aug. 4, 2014.

(51) Int. Cl.
*B23K 1/00* (2006.01)
*B23K 3/00* (2006.01)
(Continued)

(52) U.S. Cl.
CPC ............ *H05K 3/34* (2013.01); *B23K 1/0016* (2013.01); *B23K 3/033* (2013.01); *B23K 3/08* (2013.01);
(Continued)

(58) Field of Classification Search
CPC . B23K 3/033; B23K 3/0478; H05K 2203/163; H01L 2224/81815
(Continued)

(56) References Cited

U.S. PATENT DOCUMENTS 4,418,268 A    11/1983    Munshaw
4,792,078 A    12/1988    Takahashi
(Continued)

FOREIGN PATENT DOCUMENTS

CN    102209441    10/2011
DE    41 43 545 C2    9/2002
(Continued)

OTHER PUBLICATIONS

Patent Examination Report No. 1 issued in parallel Australian Application No. 2015205882; 6 pages.
(Continued)

*Primary Examiner* — Erin Saad
(74) *Attorney, Agent, or Firm* — Lewis Roca Rothgerber Christie LLP (57) ABSTRACT

A soldering iron station and a method thereof for a soldering joint connection validation, the method including: identifying a type of the soldering cartridge being used; performing a preliminary validation by measuring the soldering tip temperature, after the soldering event has started; monitoring the power level delivered to the soldering tip to detect liquidus occurrence; determining the thickness of an intermetallic component (IMC) of the soldering joint; determining whether the thickness of the IMC is within a predetermined rage, within a predetermined cooling time period; and indicating that a reliable soldering joint connection is formed, when the thickness of the IMC is within the predetermined rage, within the predetermined cooling time period.

20 Claims, 7 Drawing Sheets

(51) Int. Cl.
  *B23K 3/02* (2006.01)
  *B23K 31/00* (2006.01)
  *B23K 31/02* (2006.01)
  *H05K 3/34* (2006.01)
  *B23K 3/08* (2006.01)
  *B23K 3/03* (2006.01)
  *B23K 31/12* (2006.01)
  *H05K 3/22* (2006.01)

(52) U.S. Cl.
  CPC ............. *B23K 31/125* (2013.01); *H05K 3/225* (2013.01); *H05K 2203/163* (2013.01)

(58) Field of Classification Search
  USPC ......... 228/51, 55, 8, 102, 103, 119, 233.2, 9
  See application file for complete search history.

(56) References Cited

U.S. PATENT DOCUMENTS

| | | |
|---|---|---|
| 4,801,069 A | 1/1989 | Ankrom et al. |
| 5,223,689 A | 6/1993 | Cowell et al. |
| 5,495,093 A | 2/1996 | Griffith |
| 5,928,536 A | 7/1999 | Lee |
| 6,563,087 B1 | 5/2003 | Yokoyama et al. |
| 6,580,050 B1 | 6/2003 | Miller et al. |
| 6,946,623 B2 | 9/2005 | Evanyk |
| 7,044,354 B2 | 5/2006 | Tetuo et al. |
| 7,780,060 B2 | 8/2010 | Fitzsimmons et al. |
| 8,274,011 B2 | 9/2012 | Masaki |
| 8,288,868 B2 | 10/2012 | Seko |
| 8,733,620 B2 | 5/2014 | Renavikar et al. |
| 9,327,361 B2 * | 5/2016 | Marino ............... B23K 3/0471 |
| 2003/0089696 A1 | 5/2003 | Yokoyama et al. |
| 2013/0039563 A1 | 2/2013 | Han et al. |
| 2016/0221098 A1 * | 8/2016 | Marino ............... B23K 3/0471 |

FOREIGN PATENT DOCUMENTS

| | | |
|---|---|---|
| JP | 3-27872 A | 2/1991 |
| JP | 2000-42735 A | 2/2000 |
| JP | 2008-45956 | 2/2008 |
| JP | 2008-307601 | 12/2008 |
| JP | 2009-257857 A | 11/2009 |
| JP | 2010-29888 | 2/2010 |
| WO | WO 2006/038885 A1 | 4/2006 |

OTHER PUBLICATIONS

European Search Report for corresponding European Patent Application No. 15179757.8, dated Feb. 23, 2016 (9 pages).

Communication together with extended European Search Report with Opinion for Application No. 15179757.8-1702 / 3000550, dated Jun. 28, 2016, 17 pages.

Notice of Preliminary Rejection dated Sep. 26, 2016 for corresponding KR Application No. 10-2015-0109543, inc. partial Englist translation, 11pp.

* cited by examiner

Sample    Current    Current    Liquidus detected

SOLDERING IRON WITH AUTOMATIC SOLDERING CONNECTION VALIDATION

CROSS-REFERENCE TO RELATED APPLICATIONS

This Patent Application claims the benefit of the filing date of U.S. Provisional Patent Application Ser. No. 62/033,037, filed on Aug. 4, 2014 and entitled "Connection Validation For Handheld Soldering Iron Station," the entire content of which is hereby expressly incorporated by reference.

FIELD OF THE INVENTION

The present invention relates generally to manufacturing, repair and rework of printed circuit boards (PCBs); and more particularly to a soldering iron with automatic soldering connection validation.

BACKGROUND

With the greater variety of components used on printed circuit boards (PCBs), smaller passive components and larger ICs with finer ball pitch dimensions, the demands on high quality solder joints to aid PCB assembly (PCBA) fabrication and rework have increased. Faulty solder joint has cost companies billions of dollars over the years. Many processes have been developed to reduce failure rate for wave solder systems. However, for point to point handheld soldering and rework applications, companies are purely relying on operators' skills to produce good solder joints with quality electrical connections. Regardless of how much training is provided to the operators of the soldering iron, without guidance during a soldering activity, the operators may make and repeat mistakes due to the fact that there are many factors that impact heat transfer by the soldering iron for forming a solder joint with good electrical connection. These factors include solder tip temperature, geometry of the solder tip, oxidation of the solder, human behavior, and the like.

SUMMARY

In some embodiments, the present invention is a method performed by a handheld soldering iron station for a soldering joint connection validation, the handheld soldering iron station including a soldering cartridge having a soldering tip. The method includes: identifying a type of the soldering cartridge being used by the soldering iron station and obtaining information related to the identified cartridge; determining that a soldering event has started by measuring a power level delivered to the soldering tip, within a first predetermined time period; performing a preliminary validation by measuring a soldering tip temperature, after the soldering event has started; monitoring the power level delivered to the soldering tip to detect liquidus occurrence; determining a thickness of an intermetallic component (IMC) of the soldering joint as a function of soldering time and soldering tip temperature, after detect the liquidus occurrence; determining whether the thickness of the IMC is within a predetermined range, within a predetermined cooling time period; and indicating that a reliable soldering joint connection is formed, when the thickness of the IMC is within the predetermined range, within the predetermined cooling time period.

In some embodiments, the present invention is a soldering iron station with automatic soldering joint connection validation including: a hand piece including a soldering cartridge having a soldering tip; a power supply for delivering power to the soldering tip; an indicator; and a processor including associated circuits for identifying a type of the soldering cartridge being used by the soldering iron station and obtaining information related to the identified cartridge; performing a preliminary validation by measuring a soldering tip temperature; monitoring the power level delivered to the soldering tip to detect liquidus occurrence; determining a thickness of an intermetallic component (IMC) of the soldering joint as a function of soldering time and soldering tip temperature, after detecting the liquidus occurrence; and determining whether the thickness of the IMC is within a predetermined range, within a predetermined cooling time period. The indicator indicates that a reliable soldering joint connection is formed, when the thickness of the IMC is within the predetermined range, within the predetermined cooling time period.

In some embodiments, the present invention is a method performed by a handheld soldering iron station for a soldering joint connection validation, the handheld soldering iron station including two cameras for capturing respective images of the soldering joint from different views. The method includes: capturing a 2-dimensional (2D) reference image of the soldering joint by each of the cameras, before a soldering event starts; generating a 3-dimensional (3D) reference image of the soldering joint from the captured 2D reference images; determining an amount of solder needed to fill in a barrel of a hole for a through hole component, or to fill in a surface of a barrel of a hole for a surface mount component, from the 3D reference image; capturing a 2D current image of the soldering joint by each of the cameras, after the soldering event starts; comparing a value of each pixel in each of the 2D current images to corresponding pixel values in the 2D reference images, respectively to detect any color changes of the pixels in the 2D current images due to spread of a dispensed solder, as the soldering event progresses; repeating capturing a 2D current image and comparing a value of each pixel, until all the pixels in the 2D current images are determined to be pixels of the dispensed solder to detect an occurrence of a liquidus of the dispensed solder; after detection of the occurrence of the liquidus, generating a 3D current image of the soldering joint from the last captured 2D reference image from each camera; determining volume of the dispensed solder after occurrence of the liquidus from the 3D current image; comparing the volume of the dispensed solder to the determined amount of solder needed to fill in the barrel or the surface area of the barrel to determine how much of the dispensed solder is dissipated into the barrel or on the surface area of the barrel; repeating the comparing of the volume of the dispensed solder until the dispensed solder has filed the barrel or the surface area of the barrel, within a predetermined tolerance; and activating an indicator to indicate a good connection, when the dispensed solder has filed the barrel or the surface area of the barrel within the predetermined tolerance.

In some embodiments, the present invention is a soldering iron station with automatic validation of connection of a soldering joint comprising: a hand piece including a soldering tip; a power supply for delivering power to the soldering tip; two cameras positioned at different locations, each for capturing a 2-dimensional (2D) image of the soldering joint; an indicator; and a processor including associated circuits for validation of the connection of the soldering joint. Each of the cameras captures a 2-dimensional (2D) reference image of the soldering joint by each of the cameras, before a soldering event starts; the processor generates a 3-dimensional (3D) reference image of the soldering joint from the captured 2D reference images and determines an amount of solder needed to fill in a barrel of a hole for a through hole component, or to fill in a surface of a barrel of a hole for a surface mount component, from the 3D reference image; each of the cameras captures a 2D current image of the soldering joint, after the soldering event starts, the processor compares a value of each pixel in each of the 2D current images to corresponding pixel values in the 2D reference images, respectively to detect any color changes of the pixels in the 2D current images due to spread of a dispensed solder, as the soldering event progresses, each of the cameras repeats capturing a 2D current image and the processor repeats comparing a value of each pixel, until all the pixels in the 2D current images are determined to be pixels of the dispensed solder to detect an occurrence of a liquidus of the dispensed solder, after detection of the occurrence of the liquidus, the processor generates a 3D current image of the soldering joint from the last captured 2D reference image from each camera, determines volume of the dispensed solder after occurrence of the liquidus from the 3D current image, compares the volume of the dispensed solder to the determined amount of solder needed to fill in the barrel or the surface area of the barrel to determine how much of the dispensed solder is dissipated into the barrel or on the surface area of the barrel, and repeats the comparing of the volume of the dispensed solder until the dispensed solder has filed the barrel or the surface area of the barrel within a predetermined tolerance. The soldering station further includes an indicator to indicate a good connection, when the dispensed solder has filed the barrel or the surface area of the barrel within the predetermined tolerance.

DETAILED DESCRIPTION

In some embodiments, the present invention is a soldering iron with automatic soldering connection validation. The soldering iron includes a processor, such as a microprocessor or controller, memory, input/output circuitry and other necessary electronic circuitry to perform the soldering connection validation.

In some embodiments, the processor receive various characteristics of the soldering joint and soldering iron and performs a process of calculating the intermetallic IMC thickness of solder and PCB substrate to ensure a good solder joint is formed during a soldering event. Once a good electrical connection for the solder joint is confirmed, an audio or LED indicator in the soldering iron, for example, in a hand piece, informs the operator of the formation of the good solder joint. Typically, a good solder joint formed by SAC solder and copper substrate PCB is when the intermetallic thickness is within 1 um-4 um. Accordingly, if the operator uses, for example, SAC305 (96.5% Sn, 3% Ag, 0.5% Cu) solder wire with copper substrate PCB, intermetallic thickness $Cu_6Sn_5$ is calculated by some embodiments of the present invention and the operator is notified once the intermetallic thickness of the intermetallic compound (IMC) reaches 1 um-4 um, during the soldering.

The chemical reaction between the copper substrate and the soldering iron can be shown as:

$$3Cu+Sn \rightarrow Cu_3Sn \text{ (phase 1)} \quad (1)$$

$$2Cu_3Sn+3Sn \rightarrow Cu_6Sn_5 \text{ (phase 2-IMC 1 um-4 um)} \quad (2).$$

Phase 1 of the chemical reaction is temporary (transient) and therefore is not used for determination of the quality of the solder joint.

In some embodiments, the microprocessor (or the controller) may be placed in the power supply, in the hand piece, or a stand of the soldering system. Communication with external devices, such as a local computer, a remote server, a printer and the like, may be performed at the work stand by wired and/or wireless connections, using the known wireless interfaces.

Figure 1A:
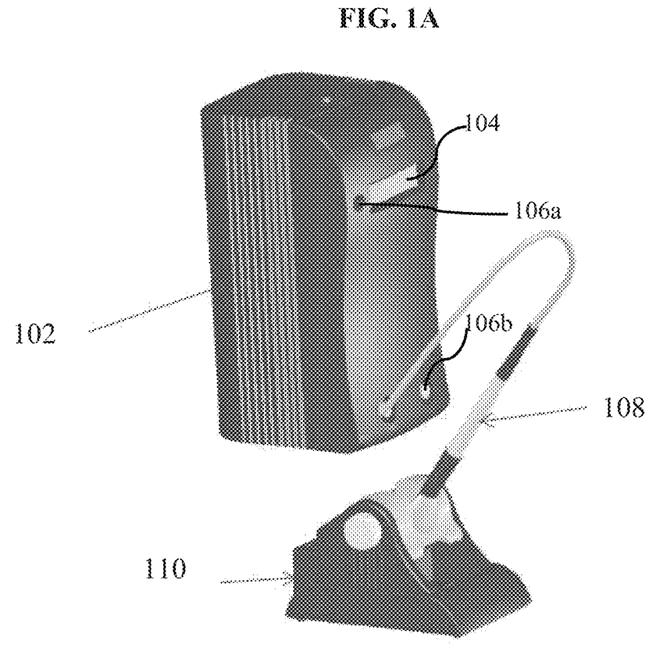
FIG. 1A depicts an exemplary handheld soldering iron, according to some embodiments of the present invention.

FIG. 1A depicts an exemplary handheld soldering iron, according to some embodiments of the present invention. As shown, the handheld soldering iron includes a power supply unit 102 including a display 104, for example an LCD display, and various indicators 106, such as LED indicators 106a and 106b. The soldering iron further includes a hand piece 108 coupled to the power supply unit 102 and a (work) stand 11 that accommodates the hand piece 108. The hand piece 108 receives power from the power supply unit 102 and heats up a soldering tip to perform the soldering on a work piece. In some embodiments, the soldering tip may include a temperature sensor to sense the tip temperature and transmit that data to the processor.

The hand piece 108 may include various indicators such as one or more LEDs and/or a buzzer on it. In some embodiment, the power supply unit 102 includes a microprocessor, memory, input/output circuitry and other necessary electronic circuitry to perform various processes.

In some embodiments, the microprocessor and the associated circuits identify what soldering cartridge is being used, validate the tip geometry, validate that the temperature and load are matched to ensure that the cartridge can produce sufficient energy to bring the load to solder melting point, detect liquidus temperature and then determine the thickness of the IMC, as described in more detail below. In some embodiments, the soldering cartridge includes the soldering tip, associated wiring, magnetic shield, heater, shaft, connector(s), a non-volatile memory (NVM), one or more sensors, and a potentiometer to measure the impedance of the tip. The liquidus temperature is the temperature above which a material is completely liquid. Liquidus temperature is mostly used for impure substances (mixtures) such as glasses, alloys and rocks. Above the liquidus temperature the material is homogeneous and liquid at equilibrium. Below the liquidus temperature, more crystals are formed in the material after a sufficient time, depending on the material.

Figure 1B:
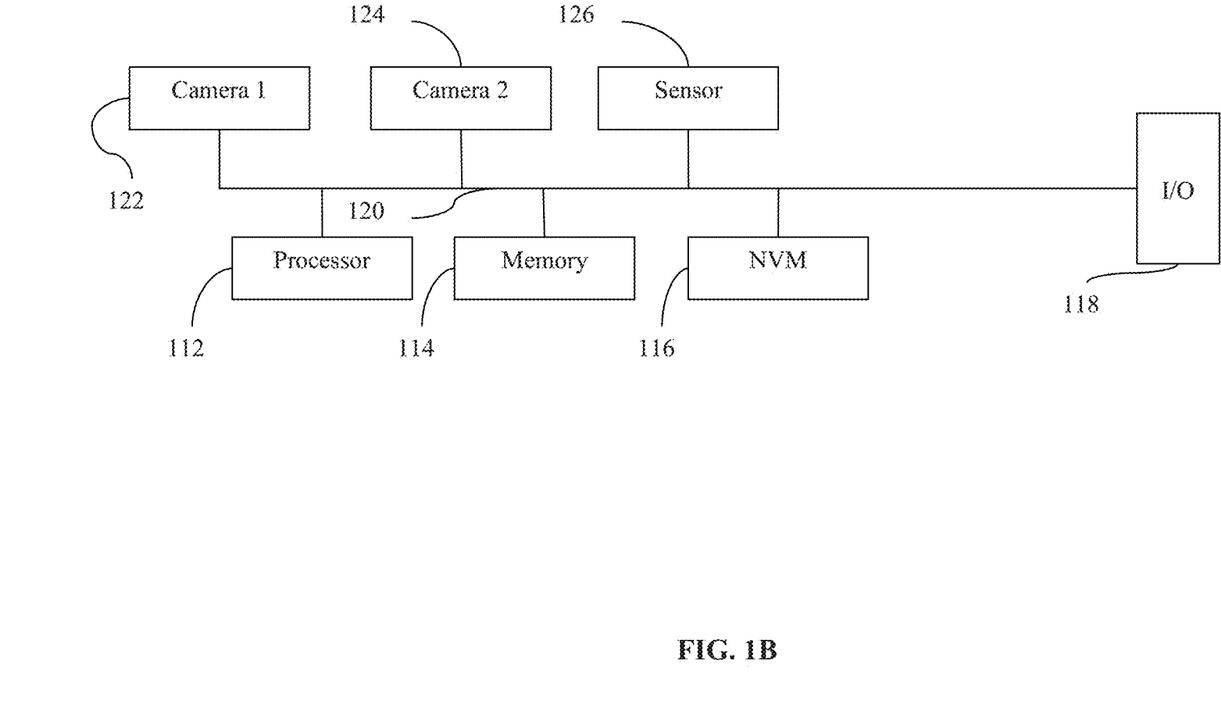
FIG. 1B is an exemplary block diagram of a processor and associated components, according to some embodiments of the present invention.

FIG. 1B is an exemplary block diagram of a processor and associated components, according to some embodiments of the present invention. As illustrated, a processor 112, a memory 114 a non-volatile memory (NVM) 116 and an I/O interface 118 are coupled to a bus 120 to comprise the processor and associated circuitry of some embodiments of the present invention. The I/O interface 118 may be a wired interface and/or a wireless interface to components external to the soldering station. Optionally, two cameras 122 and 124 are coupled to the processor and the memory via the bus 120 or the I/O interface 118 to capture images from a solder joint from different views. Additionally, an optional temperature sensor 126 for sensing the temperature of the soldering tip may be coupled to the processor 112 and the memory 114 via the bus 120 or the I/O interface 118.

Figure 2:
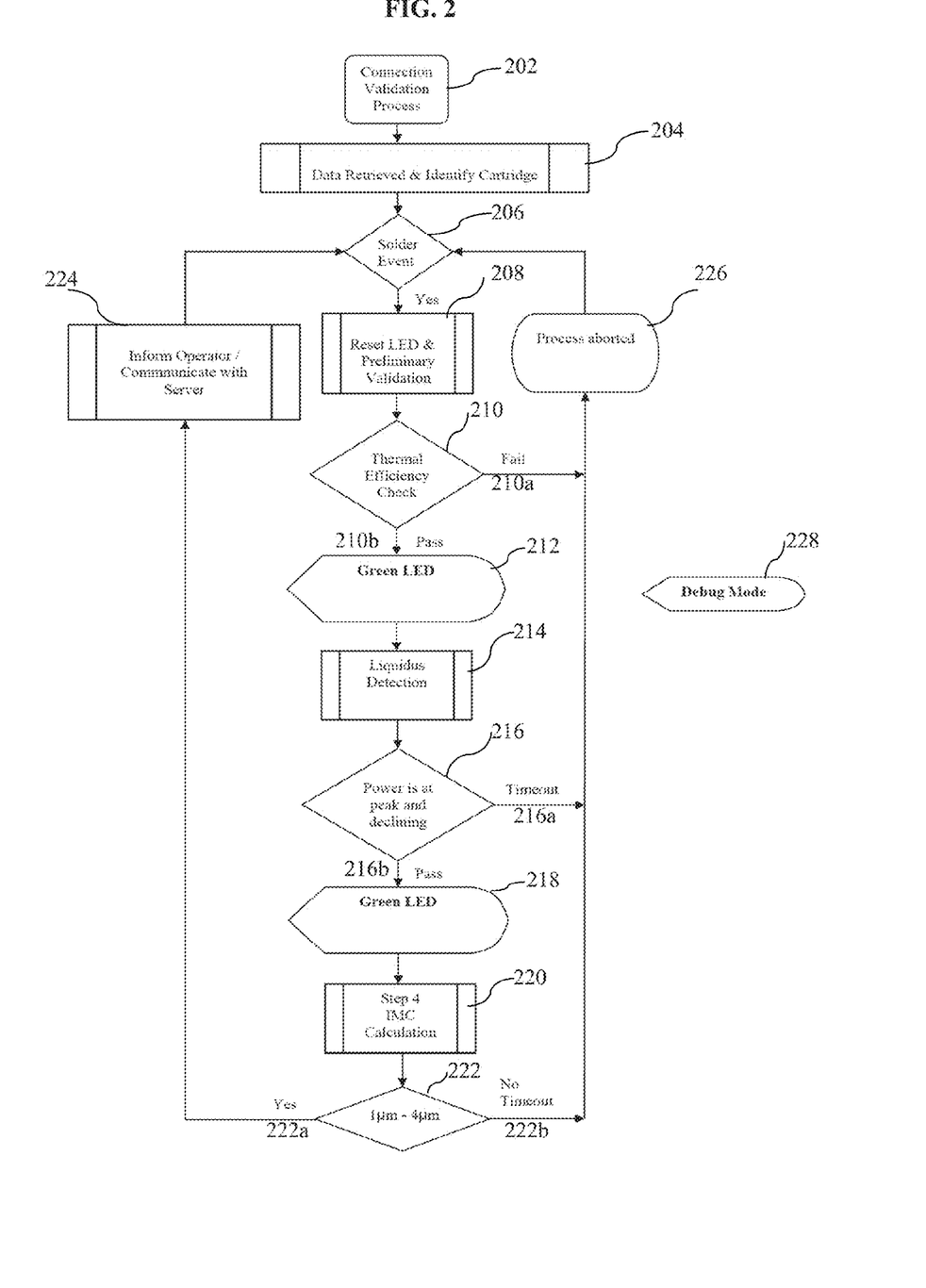
FIG. 2 shows an exemplary process flow, according to some embodiments of the present invention.

FIG. 2 shows an exemplary process flow, according to some embodiments of the present invention. As shown in block 202, The process for validating all the connections joint between the component and the PCB substrate starts. In block 204, the cartridge being used is identified and the data related to the identified cartridge is retrieved from a non-volatile memory (NVM), such as an EEPROM. In some embodiments, the NVM may be placed in the cartridge to store data related to the cartridge such as, part number, lot code, serial number, total usage, total point, tip mass/weight, tip configuration, authentication code (if any), thermal efficiency, thermal characteristic, and the like. This data may be retrieved periodically at the startup and during the operation. In some embodiments, the data may also be received and transmitted via wire or wireless methods.

In block 206, checks the power level to determine whether any soldering action is being performed, within a period of time. If no soldering action to be performed yet, the process waits in block 206. For example, a timer can be set to a predetermined time and if no action happens within that time, the process waits. However, if a soldering action to be performed, the process proceeds to an optional block 208, where the indicators are reset.

Figure 3A:
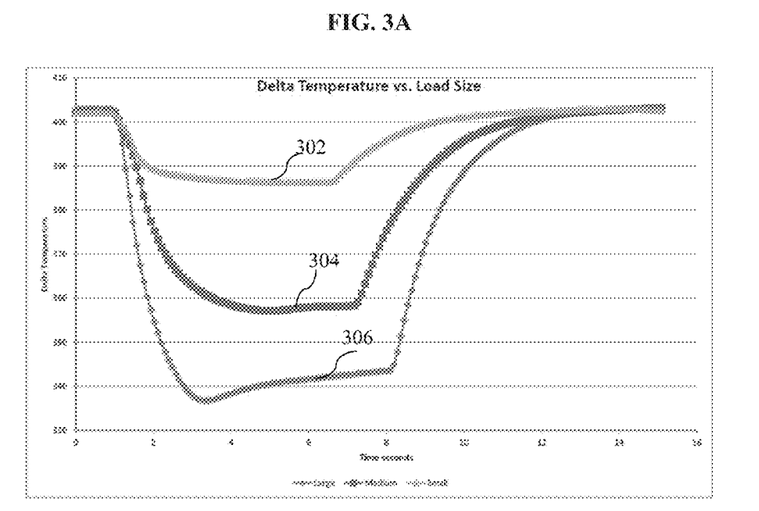
FIG. 3A shows a graph for a change in temperature of a soldering tip over time, for three given load sizes, according to some embodiments of the present invention.

FIG. 3A shows a graph for a change in temperature of a soldering tip over time, for three given load sizes. Graph 306 is for a large load size, graph 304 is for a medium load size and graph 302 shows a small load size. As illustrated in FIG. 3A, for a given tip, the heavier the load, the higher temperature drop. In some embodiments, if the tip temperature drop is greater than a predetermined value, for example, 25° C., the process is aborted since the power supply would be unable to recover fast enough to continue delivering power to the tip to maintain the temperature of the tip, within the required time to complete the soldering event (e.g., 8 seconds).

In some embodiments, the temperature drop may be detected by measuring the impedance of the tip and then determining the tip temperature by the equation (3) below. The impedance may be measured by turning off the power to the tip and measuring the voltage of the coil (in the cartridge). The impedance would then be the voltage of the coil times am Impedance Factor (K in Equation (3)), which would depend of the tip type. In some embodiments, a temperature sensor may be placed in the tip to directly read the temperature drop and communicate it to the microprocessor.

$$R_{imd} = R_{min} + R_{max}/\{1 + [k*e^\wedge(-T)]\} \quad (3).$$

Where, $R_{imd}$ is the impedance value, $R_{min}$ is a minimum value of the impedance, $R_{min}$ is a maximum value of the impedance, K is a weight factor and T is delta temperature.

Figure 3B:
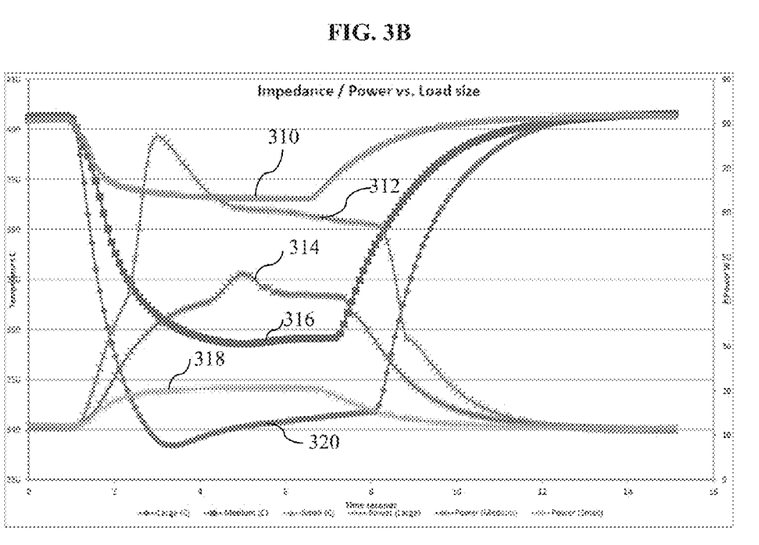
FIG. 3B depicts a graph for a change in impedance of a soldering tip over time, for three given power levels and three given temperatures, according to some embodiments of the present invention.

FIG. 3B depicts a graph for a change in impedance of a soldering tip over time, for three given power levels that are delivered by the power supply unit to the soldering tip and three given temperatures of the soldering tip. Graph 318 is for a small power, graph 312 is for a large power and graph 314 shows a medium power. Moreover, graph 310 is for a small temperature, graph 316 is for medium temperature and graph 320 is for a large temperature.

In some embodiments, the temperature drop may be detected by defining a thermal efficiency factor for each given tip geometry and heater material, as shown in Equation (4) below. If power draws higher than TE_factor, the system determines an abort in the process by, for example, turning on a red LED and/or a buzzer.

$$TE\_\text{factor} = TipMass * TipStyle * HTR\_\text{factor} * Const \quad (4),$$

where, TipMass is the copper weight (mg), which is 0.65 for a "LongReach" tip, 1 for a "Regular" tip, and 1.72 for a "Power" tip. TipStyle refers to the distance from the tip of tip to the heater in the cartridge. For example, TipStyle is 20 mm for a "LongReach" tip, 10 mm for a "Regular" tip, and 5 mm for a "Power" tip. HTR_factor is the heater temperature times a factor (e.g., 0.01), which changes based on the type of the heater. Const=4.651*10$^{-3}$ for all types of heaters. For example, the HTR_factor may be 800 F*0.01=8; 700 F*0.01=7; 600 F*0.01=6; or 500 F*0.01=5 for various heater types.

Referring back to FIG. 2, in block 210, a thermal efficiency check is performed to ensure that the tip geometry/temperature and the load are matched, based upon tip temperature drop within a predetermined time period, for example, the first 2-3 seconds. In some embodiments, the thermal efficiency check checks the heat transfer and power recovery of the soldering station with respect to the tip and the load. Each tip type has its own thermal characteristic, which is a function of the tip temperature, mass, and configuration/style. For various tip types, their thermal efficiency factors (TEs) are stored in the NVM. During the first period of time (e.g., 2-3 seconds), the power to the tip is measured and compared with the TE of the tip. If the measured power is greater than a threshold value, for example, 95%+/−10% of TE, it means that the tip is too small or the load is too large, become they require a lot of power. In this case, the thermal efficiency check fails (210*a*), the process is aborted in block 226 and optionally one or more indicators, for example, a red LED and/or a buzzer, are turned on. If the thermal efficiency check passed (210*b*), the process proceeds to the optional block 212 where a "passing" indicator, such as a green LED and/or a beep, is turned on to let the operator know that the thermal efficiency check process has passed.

In block 214, the liquidus temperature is detected based on the following heat transfer equation.

$$\Delta T = P * TR \quad (5),$$

where, $\Delta T$ is the tip temperature minus the load temperature, P is the power level, and TR is the thermal resistant between the tip and the load that may be retrieved from the NVM.

Since load temperature continues to increase until it reaches equilibrium, $\Delta T$ decreases throughout the soldering action. Also, power increases when the soldering event first starts. Therefore, TR will be decreasing, as shown below. Once liquidus occurs, TR is stabilized and thus the power P now starts decreasing, as shown below. Accordingly, to detect liquidus temperature, the change state in the power delivered to the soldering tip is observed.

$$\Delta T \downarrow = P \uparrow * TR \downarrow$$

$$\Delta T \downarrow = P \downarrow * TR \sim$$

In block 216, it is checked to see if the power is at a peak and declining. If not, the process is timed out (216a) and aborted in block 226. If the power is at a peak and declining, the process proceed to block 218 to turn on an indicator, for example, an LED and/or a beep sound. When the power is at a peak and declining, it means that the solder event is at liquidus state.

In block 220, the thickness of the IMC is determined by the following equation.

$$IMC = 1 + [k * \ln(t+1)] \quad (6),$$

where k is a weighing factor and t is solder interval time @100 ms.

Generally, the thickness of the IMC would be a function of time and temperature. When the temperature is at melting point (e.g., at 220-240° C.), it does not have a substantial impact on the thickness of the IMC. Accordingly, Equation (6) is based on only time and a fixed temperature.

Figure 4A:
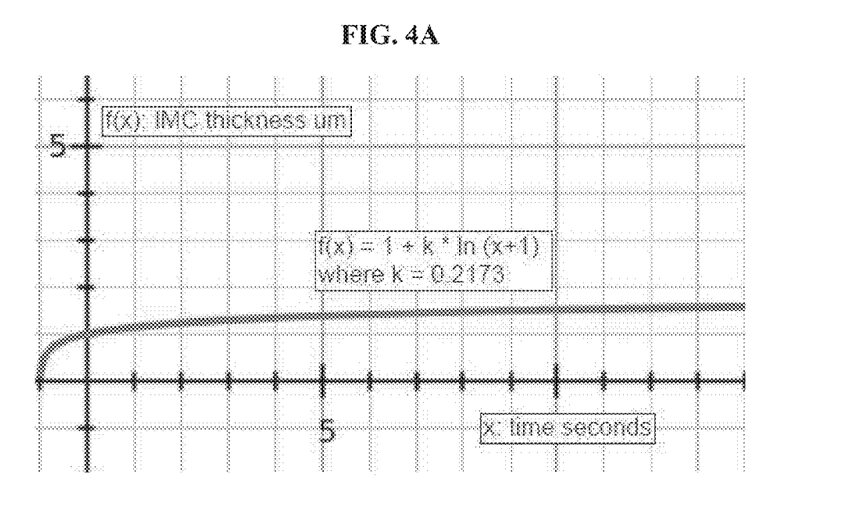
FIG. 4A illustrates a graph for the thickness of the IMC versus time, according to some embodiments of the present invention.

FIG. 4A illustrates a graph for the thickness of the IMC versus time, for k=0.2173, which is obtain by experimentation, using many soldering joint and IMC thickness measurement. As depicted in FIG. 4A, the IMC thickness increases over time.

Referring back to FIG. 2, block 222 checks to see whether within a predetermine amount of time (cooling period), the determined thickness of the IMC is within a predetermined range, for example, 1 um to 4 um. If it is, the processes proceeds to block 224, where the operator is informed. If the result of the test in block 222 is false, the process is timed out (222b) and aborted in block 226.

In some embodiments, the invention provides the operator with an indication of successful or potential non-successful joint formation, along with the ability to collect the intermetallic joint information, and the operational parameters for that particular joint for post processing. Indication can be accomplished via visual means, audible means, and/or vibration of the hand piece.

A debug mode (block 228) is used, for example, by a process engineer to keep track of the steps involved during a solder event. To enter the debug mode, a user needs to turn the debug mode on.

Figure 4B:
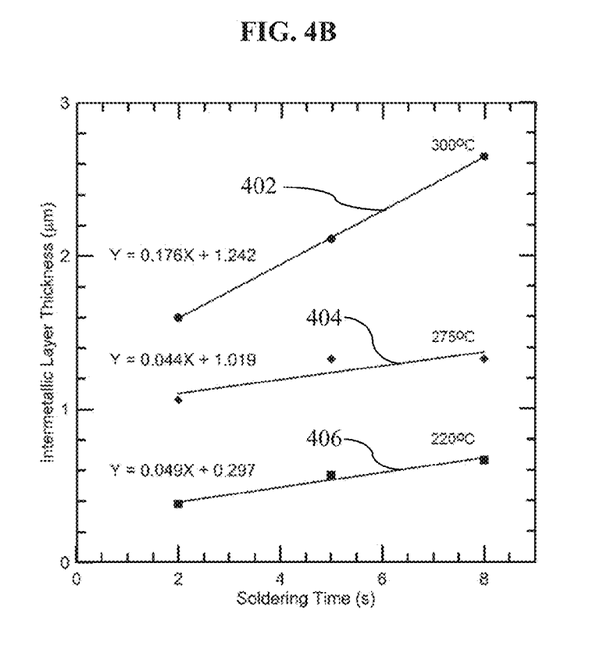
FIG. 4B illustrates a graph for the thickness for the IMC versus soldering time, according to some embodiments of the present invention.

FIG. 4B illustrates a graph for the thickness for the IMC versus soldering time. As depicted, graph 402 is for a temperature of 300° C. with Y=0.176X+1.242, graph 404 is for a temperature of 275° C. with Y=0.044X+1.019, and graph 404 is for a temperature of 220° C. with Y=0.049X+0.297, where X is the time and Y is the IMC thickness. The constant numbers are derived from multiple experimentations. As shown, a break out of the IMC thickness happens at three different temperature ranges. Since the thickness of the IMC is a function of time and temperature, as temperature rises, the IMC grows larger, as a linear function. Depending on the application, any of these curves may be used to determine the weighing factor, K, in Equation (6). For example, for a soldering application with SAC305 tip, graph 404 is used.

This way, the embodiments of the present invention ensure a good bonding and electrical connection between two metals by calculating the intermetallic thickness and therefore prevent a bad joint in early stages. Moreover, the invention provides instant feedback (by the indicators) to operators on joint quality and process issues and thus the operators have the ability to track information on joint quality for post analysis. The operators can change or select from a menu several parameters to meet certain application requirements.

In some embodiments, when a Curie temperature (point)/Smartheat™ technology, which is a self-regulated Curie temperature, is utilized, there is no requirement for calibration of the system at customer site. The Curie temperature or Curie point, is the temperature where a material's permanent magnetism changes to induced magnetism, that is, the critical point where a material's intrinsic magnetic moments change direction. The invention also provides the capability to help the operators to identify whether they are using an improper tip/cartridge combination for a soldering event In some embodiments, the invention uses at least two high resolution cameras to capture two or more 2D images, obtain a 3D image from those 2D images, use the 2D and 3D images to detect liquidus stage and then calculate the amount of solder filled through the via hole (barrel) for through hole components, or the amount solder spread out around the components for surface mount components.

Figure 5:
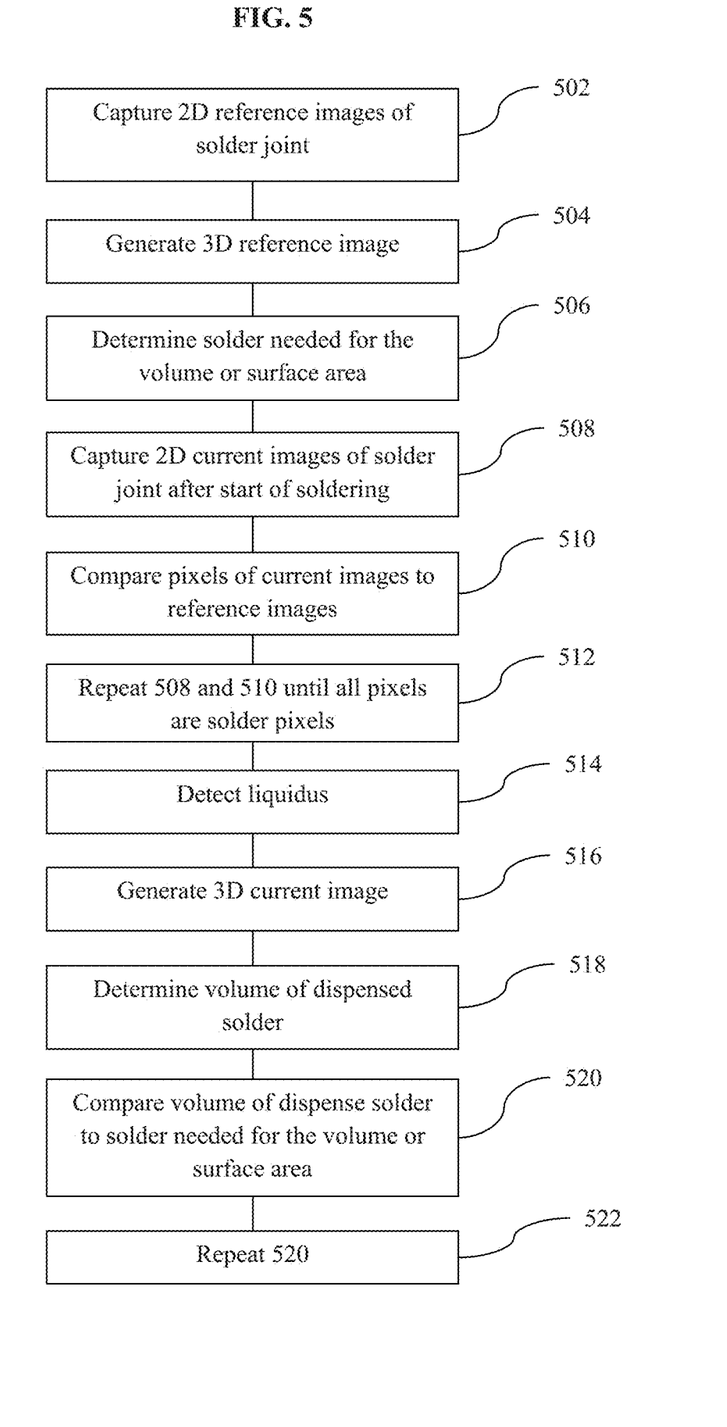
FIG. 5 is an exemplary process flow for liquidus detection and connection verification using images from a plurality of cameras, according to some embodiments of the present invention.
Figure 6A:
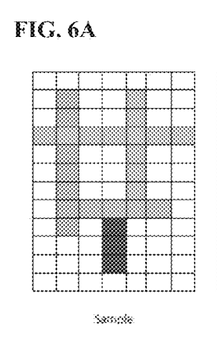
FIGS. 6A-6D show various images used for detection of liquidus, according to some embodiments of the present invention.

FIG. 5 is an exemplary process flow for liquidus detection and connection verification using images from a plurality of cameras, according to some embodiments of the present invention. At least two high resolution cameras are placed close to the soldering joint at two different locations to capture 2D images of the solder joint from two views, before and after the soldering event. The liquidus is detected from comparison of the 2D images. Then, in the case of through hole components, the volume of the through hole barrel (barrel) is determined from 3D images generated from the 2D images. In the case of surface mounted (SMT) components, the surface of the barrel on the PCB is determined from the 2D images. As shown in block 502, two images of the soldering area (joint) are captured by the two cameras, before the soldering event to generate two reference images, as depicted in FIG. 6A. In block 504, a 3D reference image of the soldering area is generated from the two reference images, before the soldering event, by well know methods.

Figure 6B:
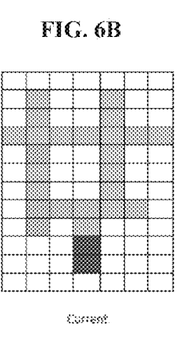

In block 506, the volume of the barrel $V_b$ for through hole and/or the surface area of the barrel $S_b$ for SMT component are determined from the 3D reference image to determine how much solder is need to fill the barrel or the surface area of the barrel. The surface of the barrel may also be determined from the 2D images, depending on the camera positions. Accordingly, the amount of solder needed to fill in the barrel or the surface of the barrel is determined, depending on the type of the component. Immediately after the soldering event is started, two current images of the soldering area is captured, in block 508. In block 510, the color value of each pixel in the 2D reference images is compared to color value of each corresponding pixel in the 2D current images, as the soldering event progresses, to detect any color changes of the pixels in the current images due to spread of the solder. Since the pixel value of the solder color is known, this the process can determine whether a pixel is a solder pixel, i.e., contains solder, as shown in FIG. 6B.

Figure 6C:
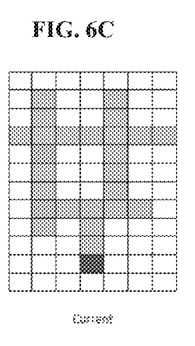
Figure 6D:
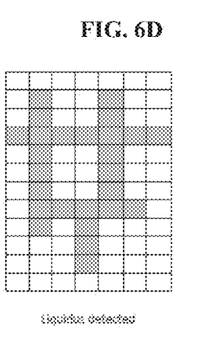

In block 512, the processes in blocks 508 (FIG. 6C) and 510 are repeated until all the pixels in the current images are determined to be pixels of the dispensed solder, that is, the liquidus is now detected, as depicted in FIG. 6D. The process in block 512 is timed out after a predetermined amount of time (e.g., 8 seconds), if not all the pixels in the current images are determined to be pixels of solder. When all the pixels in the last two current images are determined to be pixels of the dispensed solder (within a tolerance range), the liquidus is detected, in block 514.

After the detection of the liquidus, the last current image from each camera are processed to generate a 3D current image, in block 516. Then, the volume of the dispensed solder $V_s$ is determined from the 3D current image, by one or more of Equations (7) to (9), in block 518. In block 520, the calculated volume of the dispensed solder $V_s$ is compared to the determined amount of solder needed to fill in the barrel (i.e., $V_b$) or the surface area of the barrel (i.e., $S_b$) to determine how much of the dispensed solder is dissipated into the barrel or on the surface area of the barrel. This process (block 520) is repeated in block 522, until the dispensed solder has filed the barrel or the surface area of the barrel. That is, the volume of the visible dispensed solder has reached ($V_s$ Vb) or ($V_s$ $S_b$), within a predetermined tolerance range. The process in block 522 is timed out after a predetermined amount of time (e.g., 8 seconds). An indicator (e.g., a LED and/or beep) is then turn on to notify the operator that the connection is now formed by filling all of the barrel or the surface of the barrel with the dispensed solder.

Figure 7A:
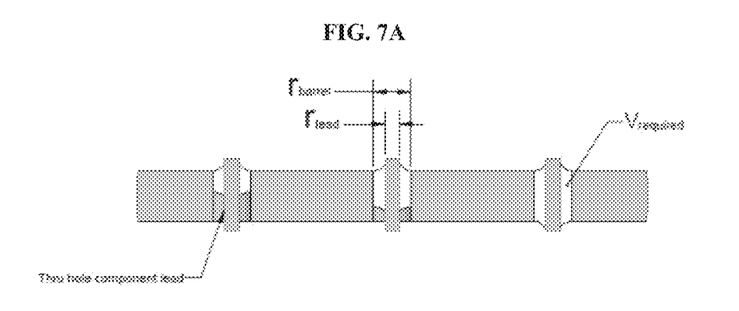
FIG. 7A shows some exemplary solder joints for through hole components, according to some embodiments of the present invention.

In other words, in the case of a through hole component, when the calculated volume reduces to a predetermined amount that is needed to fill the barrel and within a predefined tolerance for through hole component, a good solder joint is formed, as shown in FIG. 7A. In some embodiments, the calculation of the height and volume of the solder joint is performed based on the following equations.

$$V_{lead} = \pi r_{lead}^2 h \quad (7)$$

$$V_{barrel} = \pi r_{barrel}^2 h \quad (8)$$

$$V_{required} = \pi h(r_{barrel}^2 - r_{lead}^2) \quad (9)$$

Where, $V_{lead}$ is the volume of component lead; $V_{barrel}$ is the volume of through hole barrel; $V_{required}$ is the volume of solder required to fill the barrel, $r_{lead}$ is the (though hole) component lead radius; $r_{barrel}$ is through hole barrel radius; and h is the board thickness, as shown in FIG. 7A.

Figure 7B:
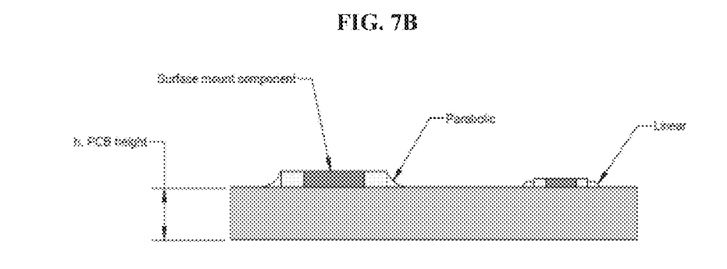
FIG. 7B depicts some exemplary solder joints for surface mount components, according to some embodiments of the present invention.

FIG. 7A shows some exemplary solder joints, the image of which is captured by the two cameras, for through hole components, according to some embodiments of the present invention. FIG. 7B shows some exemplary solder joints, the image of which is captured by the two cameras, for surface mount components, according to some embodiments of the present invention. In this case, the invention compares the height of the entire load to a predetermined reference height (a desired height) to form a parabolic or linear shape. Once the identified shape area is equivalent to a predefined percentage of the load (barrel) surface area within a predefined tolerance, a good solder is formed for the surface mount component. As shown in FIG. 7B, for a larger surface mount component, the solder joint is formed on the side of the component as a parabolic shape. However, for a smaller surface mount component, the solder joint is formed on the side of the component as a linear shape since the camera can only capture a linearly filled area due to the small size of the component.

It will be recognized by those skilled in the art that various modifications may be made to the illustrated and other embodiments of the invention described above, without departing from the broad inventive step thereof. It will be understood therefore that the invention is not limited to the particular embodiments or arrangements disclosed, but is rather intended to cover any changes, adaptations or modifications which are within the scope and spirit of the invention as defined by the appended claims.

What is claimed is:

1. A method performed by a handheld soldering iron station for a soldering joint connection validation, the handheld soldering iron station including a soldering cartridge having a soldering tip, the method comprising:
    identifying a type of the soldering cartridge being used by the soldering iron station and obtaining information related to the identified cartridge;
    determining that a soldering event has started by measuring a power level delivered to the soldering tip, within a first predetermined time period;
    performing a preliminary validation by measuring a soldering tip temperature, after the soldering event has started;
    monitoring the power level delivered to the soldering tip to detect liquidus occurrence;
    determining a thickness of an intermetallic component (IMC) of the soldering joint as a function of soldering time and soldering tip temperature, after detect the liquidus occurrence;
    determining whether the thickness of the IMC is within a predetermined range, within a predetermined cooling time period; and
    indicating that a reliable soldering joint connection is formed, when the thickness of the IMC is within the predetermined range, within the predetermined cooling time period.

2. The method of claim 1, wherein identifying a type of the soldering cartridge being used and obtaining information related to the identified cartridge comprises retrieving data from a memory within the soldering iron station, or from a memory remote from the soldering iron station.

3. The method of claim 1, wherein measuring a soldering tip temperature comprises measuring an impedance of the soldering tip and determining the soldering tip temperature as a function of the measured impedance.

4. The method of claim 1, wherein measuring a soldering tip temperature comprises defining a thermal efficiency factor for a geometry of the soldering tip and a heater material and determining the soldering tip temperature as a function of the thermal efficiency and the powered delivered to the soldering tip.

5. The method of claim 1, wherein the liquidus occurrence is detected when the monitored power is declining from a peak.

6. The method of claim 1, wherein the predetermined range of the thickness of the IMC is 1 μm-4 μm.

7. The method of claim 1, further comprising performing a thermal efficiency check and aborting the method when the thermal efficiency check fails.

8. A soldering iron station with automatic soldering joint connection validation comprising:
    a hand piece including a soldering cartridge having a soldering tip;

a power supply for delivering power to the soldering tip;
an indicator; and
a processor including associated circuits for identifying a type of the soldering cartridge being used by the soldering iron station and obtaining information related to the identified cartridge; performing a preliminary validation by measuring a soldering tip temperature; monitoring the power level delivered to the soldering tip to detect liquidus occurrence; determining a thickness of an intermetallic component (IMC) of the soldering joint as a function of soldering time and soldering tip temperature, after detecting the liquidus occurrence; and determining whether the thickness of the IMC is within a predetermined range, within a predetermined cooling time period, wherein
the indicator indicates that a reliable soldering joint connection is formed, when the thickness of the IMC is within the predetermined range, within the predetermined cooling time period.

9. The soldering iron station of claim 8, wherein the soldering iron station further includes a non-volatile memory (NVM) for storing data related to the cartridge, and wherein the processor identifies the type of the soldering cartridge being used and obtains information related to the identified cartridge by retrieving data from the NVM.

10. The soldering iron station of claim 9, wherein data related to the cartridge stored in the NVM includes one or more of a part number, lot code, a serial number, a total usage, a total point, a tip mass/weight, a tip configuration, an authentication code, a thermal efficiency, and a thermal characteristic.

11. The soldering iron station of claim 8, further comprising a temperature sensor for measuring the soldering tip temperature.

12. The soldering iron station of claim 8, wherein the processor detects the liquidus occurrence when the monitored power is declining from a peak.

13. A method performed by a handheld soldering iron station for a soldering joint connection validation, the handheld soldering iron station including two cameras for capturing respective images of the soldering joint from different views, the method comprising:
capturing a 2-dimensional (2D) reference image of the soldering joint by each of the cameras, before a soldering event starts;
generating a 3-dimensional (3D) reference image of the soldering joint from the captured 2D reference images;
determining an amount of solder needed to fill in a barrel of a hole for a through hole component, or to fill in a surface of a barrel of a hole for a surface mount component, from the 3D reference image;
capturing a 2D current image of the soldering joint by each of the cameras, after the soldering event starts;
comparing a value of each pixel in each of the 2D current images to corresponding pixel values in the 2D reference images, respectively to detect any color changes of the pixels in the 2D current images due to spread of a dispensed solder, as the soldering event progresses;
repeating capturing a 2D current image and comparing a value of each pixel, until all the pixels in the 2D current images are determined to be pixels of the dispensed solder to detect an occurrence of a liquidus of the dispensed solder;
after detection of the occurrence of the liquidus, generating a 3D current image of the soldering joint from the last captured 2D reference image from each camera;
determining volume of the dispensed solder after occurrence of the liquidus from the 3D current image;
comparing the volume of the dispensed solder to the determined amount of solder needed to fill in the barrel or the surface area of the barrel to determine how much of the dispensed solder is dissipated into the barrel or on the surface area of the barrel;
repeating the comparing of the volume of the dispensed solder until the dispensed solder has filled the barrel or the surface area of the barrel, within a predetermined tolerance; and
activating an indicator to indicate a good solder joint connection, when the dispensed solder has filled the barrel or the surface area of the barrel within the predetermined tolerance.

14. The method of claim 13, wherein comparing a value of each pixel in each of the 2D current images comprises comparing a color value of each pixel in each of the 2D current images to corresponding pixel color values in the 2D reference images, respectively in relation to a known color pixel value of solder.

15. The method of claim 14, wherein detection of the occurrence of the liquidus of the dispensed solder is determined when all of the pixel color values in the last two 2D current images are equal to the known color pixel value of solder, within a tolerance range.

16. The method of claim 13, further comprising aborting the method when within a predetermined time period, not all the pixels in the 2D current images are determined to be pixels of the dispensed solder.

17. The method of claim 13, further comprising aborting the method when within a predetermined time period, the dispensed solder has not filled the barrel or the surface area of the barrel within said predetermined tolerance.

18. A soldering iron station with automatic validation of connection of a soldering joint comprising:
a hand piece including a soldering tip;
a power supply for delivering power to the soldering tip;
two cameras positioned at different locations, each for capturing a 2-dimensional (2D) image of the soldering joint;
an indicator; and
a processor including associated circuits for validation of the connection of the soldering joint, wherein
each of the cameras captures a 2-dimensional (2D) reference image of the soldering joint by each of the cameras, before a soldering event starts,
the processor generates a 3-dimensional (3D) reference image of the soldering joint from the captured 2D reference images and determines an amount of solder needed to fill in a barrel of a hole for a through hole component, or to fill in a surface of a barrel of a hole for a surface mount component, from the 3D reference image,
each of the cameras captures a 2D current image of the soldering joint, after the soldering event starts,
the processor compares a value of each pixel in each of the 2D current images to corresponding pixel values in the 2D reference images, respectively to detect any color changes of the pixels in the 2D current images due to spread of a dispensed solder, as the soldering event progresses,
each of the cameras repeats capturing a 2D current image and the processor repeats comparing a value of each pixel, until all the pixels in the 2D current images are determined to be pixels of the dispensed solder to detect an occurrence of a liquidus of the dispensed solder, after detection of the occurrence of the liquidus, the processor generates a 3D current image of the soldering joint from the last captured 2D reference image from each camera, determines volume of the dispensed solder after occurrence of the liquidus from the 3D current image, compares the volume of the dispensed solder to the determined amount of solder needed to fill in the barrel or the surface area of the barrel to determine how much of the dispensed solder is dissipated into the barrel or on the surface area of the barrel, and repeats the comparing of the volume of the dispensed solder until the dispensed solder has filled the barrel or the surface area of the barrel within a predetermined tolerance; and an indicator to indicate a good solder joint connection, when the dispensed solder has filled the barrel or the surface area of the barrel within the predetermined tolerance.

19. The soldering iron station of claim 18, wherein the processor compares a color value of each pixel in each of the 2D current images to corresponding pixel color values in the 2D reference images, respectively in relation to a known color pixel value of solder.

20. The soldering iron station of claim 19, wherein the processor detects the occurrence of the liquidus of the dispensed solder when all of the pixel color values in the last two 2D current images are equal to the known color pixel value of solder, within a tolerance range.

* * * * *

UNITED STATES PATENT AND TRADEMARK OFFICE
CERTIFICATE OF CORRECTION

| | | |
|---|---|---|
| PATENT NO. | : 9,516,762 B2 | Page 1 of 1 |
| APPLICATION NO. | : 14/794678 | |
| DATED | : December 6, 2016 | |
| INVENTOR(S) | : Kenneth D. Marino et al. | |

It is certified that error appears in the above-identified patent and that said Letters Patent is hereby corrected as shown below:

On the Title Page

Item (57) Abstract, Line 10        Delete "rage",
Insert --range--

Item (57) Abstract, Line 13        Delete "rage",
Insert --range--

In the Claims

Column 10, Line 32, Claim 1        Delete "detect",
Insert --detecting--

Signed and Sealed this
Ninth Day of January, 2018

Joseph Matal
*Performing the Functions and Duties of the*
*Under Secretary of Commerce for Intellectual Property and*
*Director of the United States Patent and Trademark Office*